United States Patent
Barritt et al.

(10) Patent No.: US 12,023,056 B2
(45) Date of Patent: Jul. 2, 2024

(54) MEDICAL DEVICE

(71) Applicant: TERUMO KABUSHIKI KAISHA, Tokyo (JP)

(72) Inventors: John Bertram Barritt, San Jose, CA (US); Yuichi Tada, Santa Clara, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 118 days.

(21) Appl. No.: 17/401,286

(22) Filed: Aug. 12, 2021

(65) Prior Publication Data

US 2022/0047288 A1     Feb. 17, 2022

Related U.S. Application Data

(60) Provisional application No. 63/064,600, filed on Aug. 12, 2020.

(51) Int. Cl.
| | |
|---|---|
| *A61B 17/22* | (2006.01) |
| *A61B 17/3207* | (2006.01) |
| *A61B 17/00* | (2006.01) |

(52) U.S. Cl.
CPC ......... *A61B 17/22031* (2013.01); *A61B 17/320758* (2013.01); *A61B 2017/00862* (2013.01)

(58) Field of Classification Search
CPC .. A61B 17/320068; A61B 2017/00862; A61B 17/320758; A61B 2217/005
See application file for complete search history.

(56) References Cited

U.S. PATENT DOCUMENTS

| | | | |
|---|---|---|---|
| 6,669,710 B2 * | 12/2003 | Moutafis | A61B 17/320758 606/167 |
| 8,475,484 B2 | 7/2013 | Wulfman et al. | |
| 8,939,345 B2 * | 1/2015 | Isobe | B23B 39/14 227/179.1 |
| 9,700,347 B2 * | 7/2017 | Shiber | A61B 17/320758 |
| 10,258,366 B2 * | 4/2019 | Nakano | A61B 17/221 |
| 10,433,868 B2 | 10/2019 | McGuckin, Jr. et al. | |
| 2018/0055535 A1 * | 3/2018 | Tada | A61M 25/0023 |

FOREIGN PATENT DOCUMENTS

WO    WO-2019189078 A1 *   10/2019    ....... A61B 17/32002

OTHER PUBLICATIONS

Merriam-Wester online dictionary, "busher" definition, accessed on Mar. 9, 2023, https://www.merriam-webster.com/dictionary/busher. (Year: 2023).*
Wikipedia Online Encyclopedia, "Plain bearing," accessed Oct. 19, 2023, https://en.wikipedia.org/wiki/Plain_bearing.*

\* cited by examiner

*Primary Examiner* — Kathleen S Holwerda
*Assistant Examiner* — Daniel Icet
(74) *Attorney, Agent, or Firm* — Kim & Stewart LLP

(57) ABSTRACT

A medical device for cutting substances inside a body lumen includes a flexible and elongated drive shaft including a distal portion and a proximal portion, a cutting member connected to the distal portion of the drive shaft to be rotatable with the drive shaft, and a hub located at the proximal portion and supporting the drive shaft, the hub including a first bearing mounted on the drive shaft and an elastic ring that is made of an elastic material on an outer periphery of the first bearing.

14 Claims, 10 Drawing Sheets

MEDICAL DEVICE

CROSS REFERENCE TO RELATED APPLICATIONS

This patent application claims priority to U.S. Provisional Patent Application No. 63/064,600, titled "MEDICAL DEVICE" and filed on Aug. 12, 2020. This application is herein incorporated by reference in its entirety.

TECHNICAL FIELD

Embodiments of the present disclosure relate to a medical device.

BACKGROUND

Medical devices that have a catheter including a rotatable drive shaft and a cutting member are widely used to remove a substance such as a blood clot and a thrombus from a body lumen. Such medical devices have a motor for generating torque and a hub for storing mechanism to transmit the generated torque to the cutting member through the drive shaft.

Generally, the proximal end of the drive shaft is housed in the hub and is formed of a plurality of pipes having slightly different diameters. It is inevitable for those pipes to be formed such that a center axis of one pipe (or a portion of a single pipe) and a center axis of another pipe (or the other portion of the single pipe) are misaligned because of manufacturing process of joining pipes. This misalignment can lead to wobbling and vibration when the motor rotates at high speed, resulting in increased friction, poor performance, and/or damage of the medical device.

A typical way to improve alignment and smooth rotation of such a drive shaft is the use of a bearing. In order for a bearing to effectively provide the alignment and smooth rotation desired, the bearing must snuggly fit to both the rotatable shaft and the static hub. If the bearing does not fit snuggly to either component, its effectiveness is reduced.

SUMMARY OF THE INVENTION

In an embodiment, a medical device for cutting substances inside a body lumen includes a flexible and elongated drive shaft including a distal portion and a proximal portion, a cutting member connected to the distal portion of the drive shaft to be rotatable with the drive shaft, and a hub located at the proximal portion and supporting the drive shaft. The hub includes a first bearing mounted on the drive shaft and an elastic ring that is made of an elastic material on an outer periphery of the first bearing.

DESCRIPTION OF EMBODIMENTS

The following detailed description describes a medical device for cutting substances inside a body lumen according to embodiments of the present invention. In the present specification, a side of the medical device which is inserted into a body lumen is defined as a distal side, and a hand-side of the medical device which is operated by an operator is defined as a proximal side.

Figure 1:
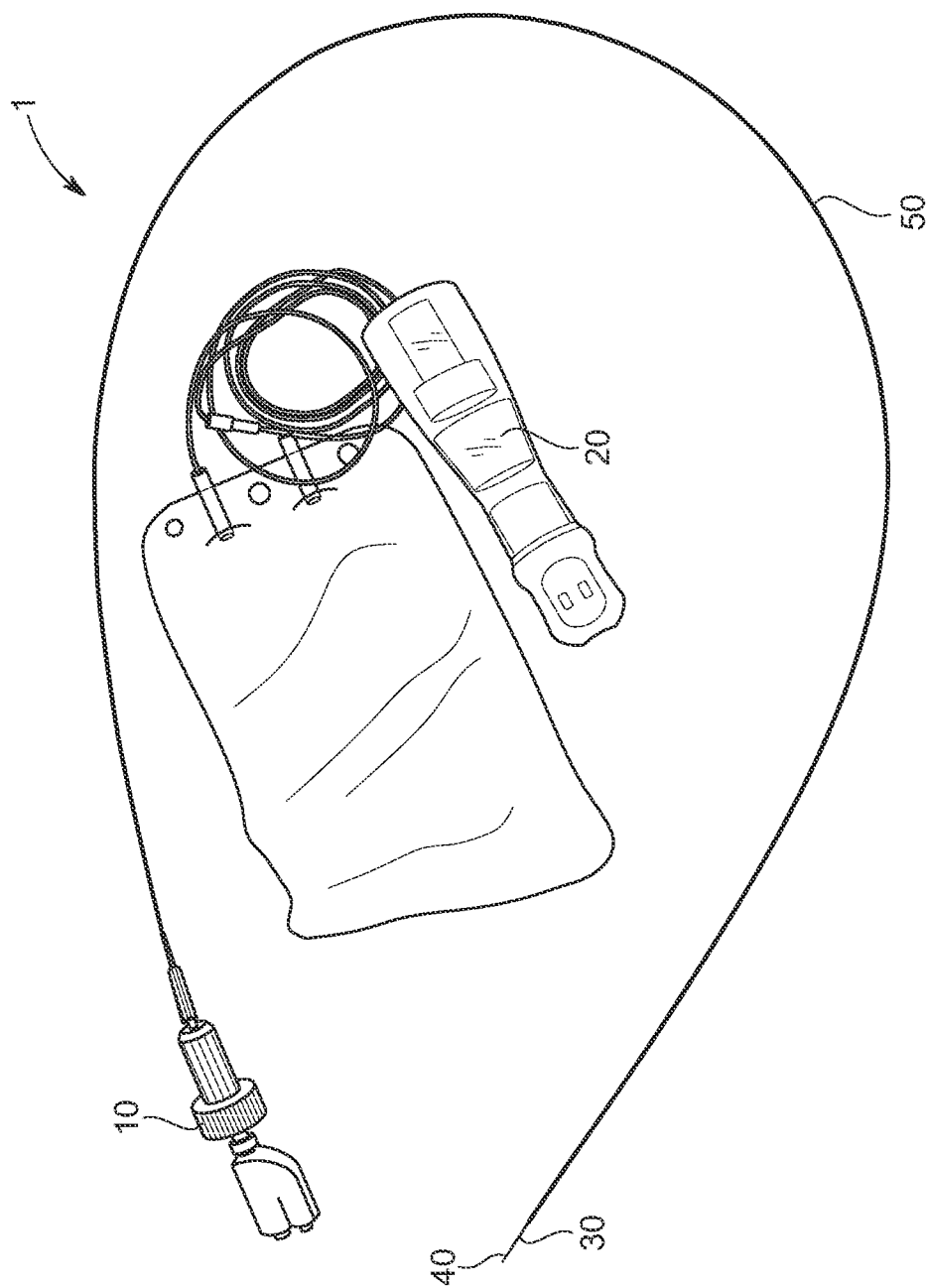
FIGS. 1 and 2 depict a medical device including a hub and a detachable handle according to one embodiment.
Figure 2:
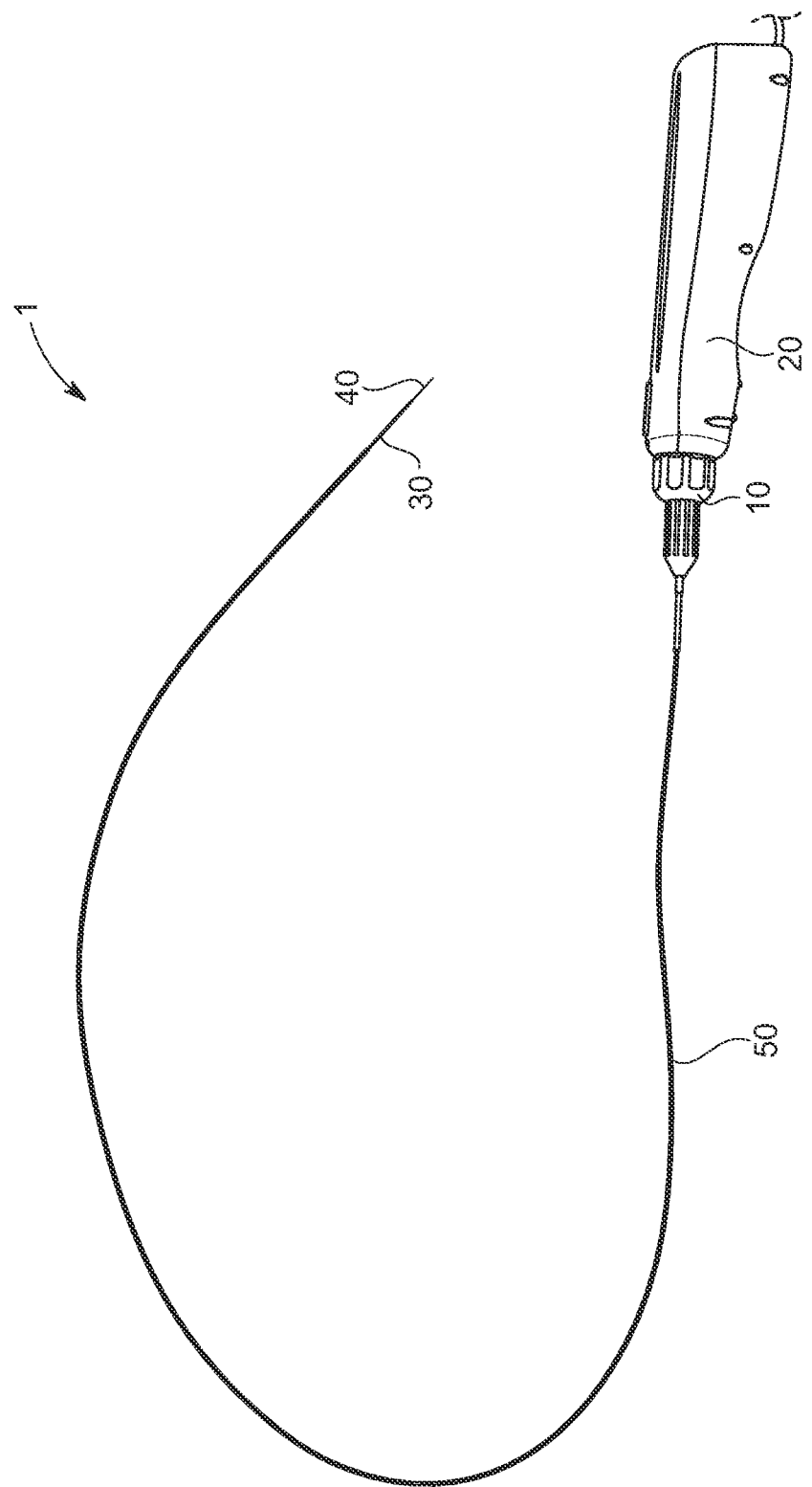

FIGS. 1 and 2 depict a medical device 1 in one embodiment. As shown in the figures, the medical device 1 includes a hub 10 for housing rotating and aspiration mechanisms and a handle 20 including a torque generating element such as a motor and held by an operator. The medical device 1 further includes an elongated drive shaft 30, a cutting member 40, and an outer shaft 50, which are inserted into a body lumen.

The drive shaft 30 has the characteristics of being flexible and capable of transmitting rotational power applied from the proximal side to the distal side. Specifically, the drive shaft 30 transmits the rotational torque generated by the torque generating element to the cutting member 40. The drive shaft 30 is formed with an aspiration lumen through which substances that have been cut by the cutting member 40 are moved to the proximal side. The drive shaft 30 penetrates the outer shaft 50, and the cutting member 40 is fixed to a distal portion of the drive shaft 30. The proximal end portion of the drive shaft 30 is positioned inside of the hub 10.

The drive shaft 30 has a distal opening at which the aspiration lumen opens, at a distal end thereof. The distal opening is an entrance into which the cut substances enter. The proximal end portion of the drive shaft 30 is connected to an aspiration drill 104 (described later) through which the substances that have entered the drive shaft 30 are discharged.

In one embodiment, the drive shaft 30, the cutting member 40, and the outer shaft 50 make up a catheter. The medical device 1 may further include a guide member (not shown) at the distal end of the drive shaft 30 for the operator to control movement of the catheter inside the body lumen.

The handle 20 is detachable from the hub 10 so as to be reusable in multiple medical procedures. When a medical procedure is performed, the handle 20 is attached to the hub 10 so that the drive shaft 30 and the cutting member 40 can rotate according to the torque generated by the motor housed in the handle 20. Thereafter, the drive shaft 30 and the cutting member 40 are inserted into a body lumen, e.g., a vein, using a guide wire. In one embodiment, the hub 10 and the handle 20 may be integrated into a single component so as not to be detachable.

Further details of the aspiration and torque generating mechanisms are described in U.S. application Ser. No. 16/998,824, the entire contents of which are incorporated by reference herein.

Figure 3:
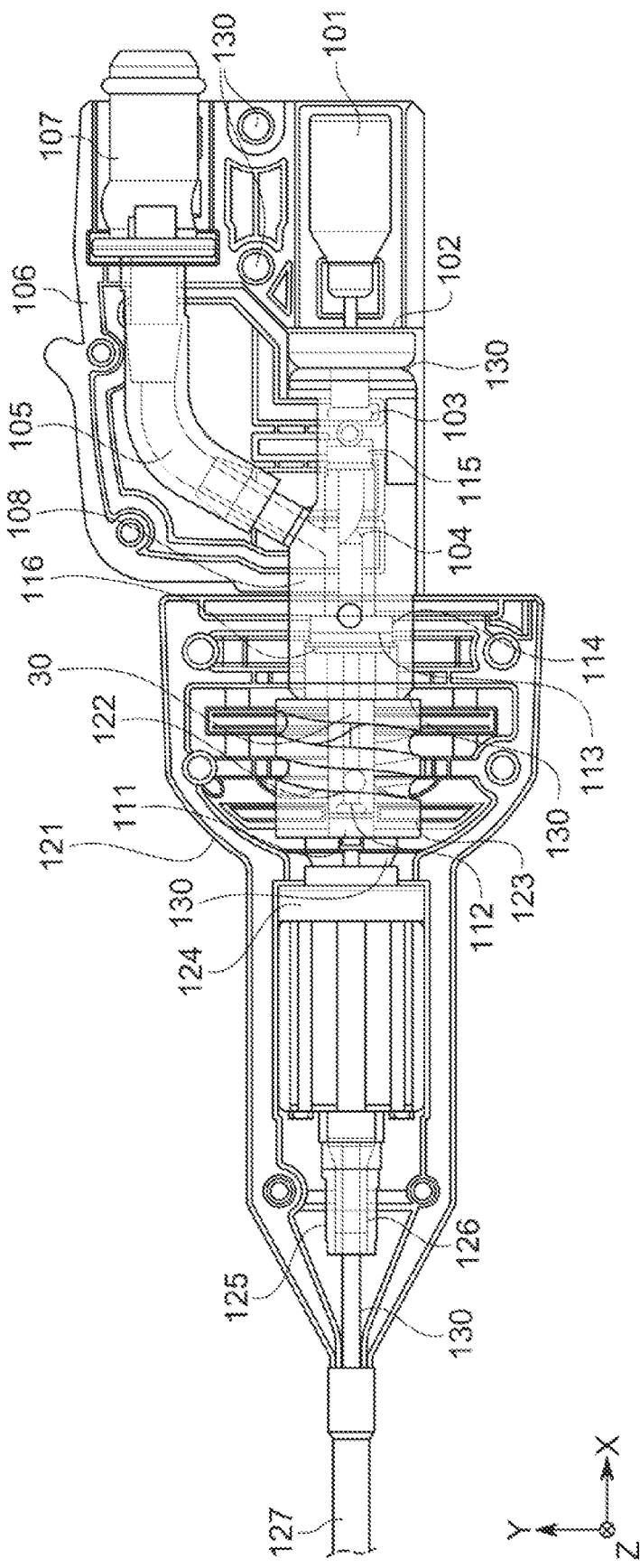
FIGS. 3 and 4 depict an internal structure of a hub according to one embodiment.
Figure 4:
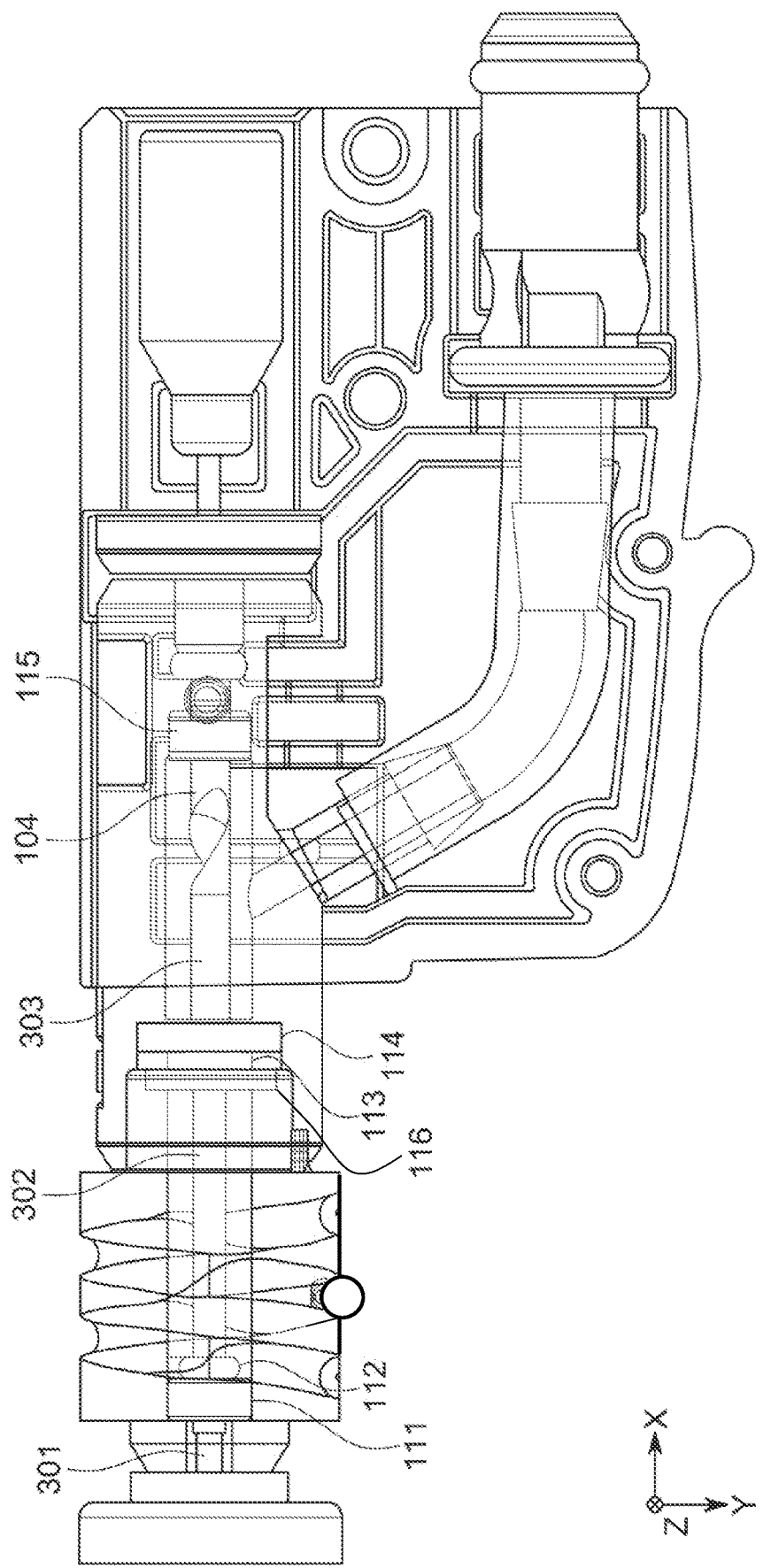

FIGS. 3 and 4 depict the internal structure of the hub 10 according to one embodiment.

As shown in FIG. 3, the proximal end of the drive shaft 30 is inserted into the hub 10 to be connectable to the motor in the handle 20 via a motor driver coupler 101 and a T-port 102.

Substances that have been removed from a body lumen are aspirated through the single flute aspiration drill 104, an aspiration tube 105, an aspiration hub 106, and an aspiration connector 107. Movement of the aspiration drill 104 along a longitudinal direction thereof (i.e., X-axis in FIG. 3) is prevented by an O-ring 103. In one embodiment, the aspiration drill 104 is integrated into the drive shaft 30 to form a proximal end portion of the drive shaft 30 inside the hub 10. In another embodiment, the aspiration drill 104 is connected to a pipe, which is a proximal end of the drive shaft 30. The proximal end portion of the drive shaft 30 or the aspiration drill 104 extends to the inside of the motor driver coupler 101.

In addition to the aspiration drill 104, as shown in FIG. 4, a plurality of pipes 301, 302, and 303 are joined at the proximal end portion of the drive shaft 30. Hereinafter, those pipes are referred to as a drive pipe 301, a joint pipe 302, and a joint pipe 303 from the distal end of the drive shaft 30 for purposes of illustration. In this disclosure, the term "pipe" means not only a component having a hollow body but a component having a hollow, a part of which is filled with some material. Those pipes 301, 302, and 303 have a substantially similar diameter. Alternatively, the diameters of the pipes 301, 302, and 303 may be different such that the diameter of the pipe 303 is larger than the pipe 302, and the diameter of the pipe 302 is larger than the pipe 301.

The drive pipe 301 extends to the cutting member 40 attached to the distal end portion of the drive shaft 30. In one embodiment, the drive pipe 301, the joint pipe 302, the joint pipe 303, and the aspiration drill 104 are joined and integrated into a single component at the proximal end of the drive shaft 30 inside the hub 10. In another embodiment, a single pipe, two pipes, or four or more pipes may be formed at the proximal end of the drive shaft 30 and connected to the aspiration drill 104. A joint pipe and the aspiration drill 104 may be integrated into a single pipe. Hereinafter, the pipes 301-303 and the aspiration drill 104 are described as a part of the drive shaft 30, i.e., the proximal end portion of the drive shaft 30.

For obtaining smooth rotation of the drive shaft 30 inside the hub 10 and preventing vibration, the hub 10 includes three bearings 111, 113, and 115 and two O-rings 112 and 114 in the hub 10. The details of those components are described later.

With reference back to FIG. 3, the hub 10 further includes a torque knob 121, which is used by the operator to manually rotate a guide member (not shown) attached at the proximal end of the outer shaft 50 and independently rotatable from the drive shaft 30 and the cutting member 40. The torque knob 121 is connected to a torque unit 124 which is formed of a flexible material and generates torque in response to the rotation of the torque knob 121. The generated torque is transmitted from the torque knob 121 to the guide member via the outer shaft 50. The torque knob 121 and the torque unit 124 are connected via a T-port 108. The T-port 108 contacts the inner surface of the hub 10 and includes a T-port distal cap 123. The T-port distal cap 123 has a groove on the outer surface thereof. The torque knob 121 also has a groove such that a 2 mm ball 122 moves between the grooves of the T-port distal cap 123 and the torque knob 121 for smooth rotation of the torque knob 121. The T-port 108 connects the aspiration connector 107 to an aspiration device, e.g., an aspiration pump and a syringe.

The hub 10 further includes, at the distal end thereof, a luer lock connector 125, a centering tube 126 for centering the drive shaft 30, and an anti-kink protector 127 to prevent the drive shaft 30 from kinking. Glue 130 is applied to the inner surface of the hub 10 and other components to secure their installation.

With reference to FIGS. 5 through 8, the bearings 111, 113, and 115 and the O-rings 112 and 114 are described. In one embodiment, each of the bearings 111, 113, and 115 is disposed at a position at which two pipes of the drive shaft 30 are joined. Those bearings 111, 113, and 115 and the O-rings 112 and 114 can effectively minimize vibrations that may occur due to the manufacturing variations of the hub 10, which is injection molded.

When the hub 10 is injection molded, a "draft" or a clearance is formed on an interior surface 500 of the hub 10 so that the hub 10 can be released from the mold. This draft can result in the loss of the snug fit between the outside of each of the bearings and the interior surface 500 of the hub 10. Each bearing will lose the snug fit if it is needed in a location where the draft requirement results in a larger diameter of the interior surface 500 of the hub 10 so that the hub 10 cannot snuggly fit the bearing, or if the bearing can move due to vibration into such a location.

Specifically, the bearing 111 can move proximally into an area of the draft, thus losing its efficacy. Restricting the motion of this bearing 111 along the rotation axis of the drive shaft 30 is achieved by the O-ring 112, which is made of an elastic material, e.g., rubber. The O-ring 112 is snuggly fit onto the drive shaft 30 and maintains the position of the bearing 111 on the hub 10.

Additionally, the O-ring 114 is disposed around the bearing 113 to provide a snug fit within the hub 10. The O-ring 114 mounted on the outer periphery of the bearing 113 and occupies the space between the bearing 113 and the interior surface 500 of the hub 10 to provide the snug fit within the hub 10. As a result, the O-ring 114 restricts the wobble movement of the bearing 113 at this location and also serves as a dampener to reduce vibration and wobble of the medical device 1.

Figure 5:
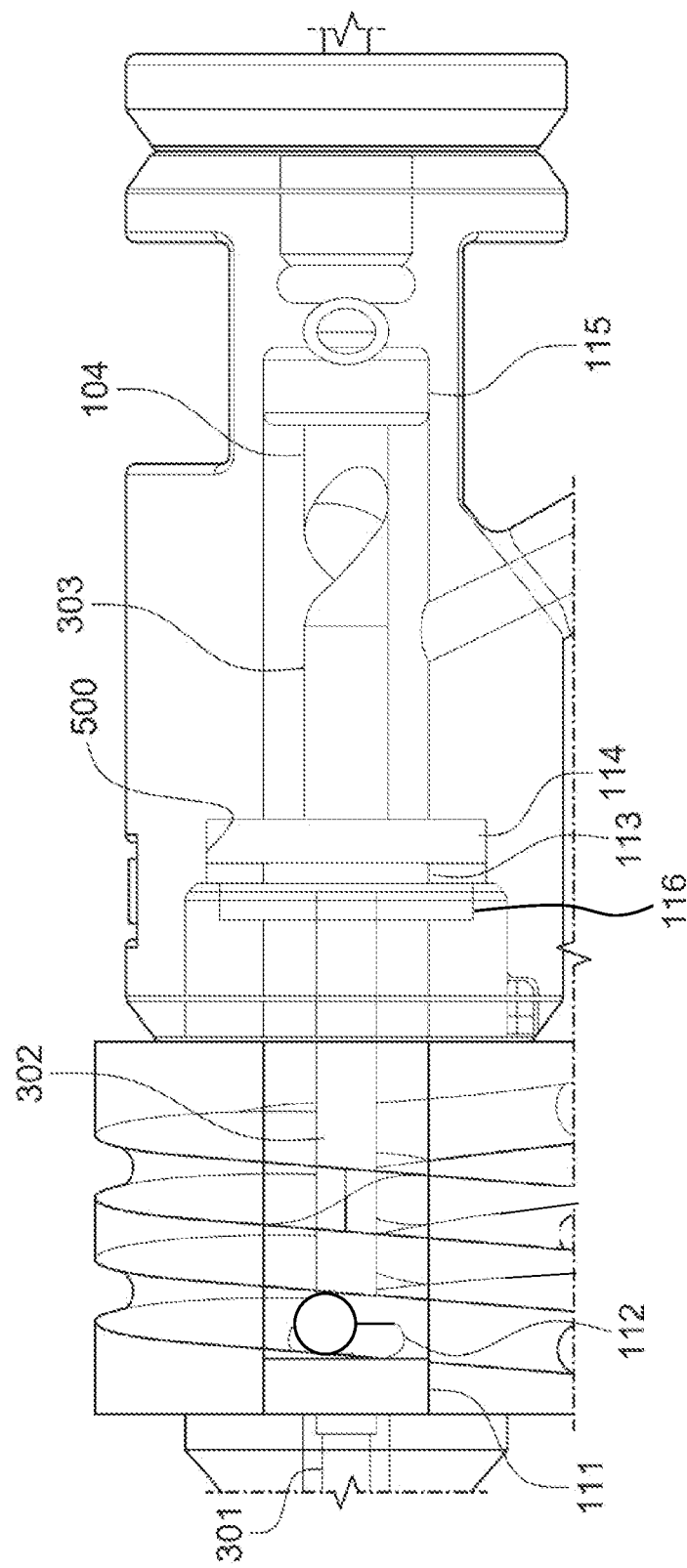
FIGS. 5 and 6 depict cross-sectional diagrams of a hub according to one embodiment.

As illustrated in FIG. 5, an O-ring is not disposed around the bearing 115, because at that location of the hub 10, the bearing 115 snuggly fits inside the hub 10. Nevertheless, in some embodiments, an O-ring may be disposed around the bearing 115.

Figure 6:
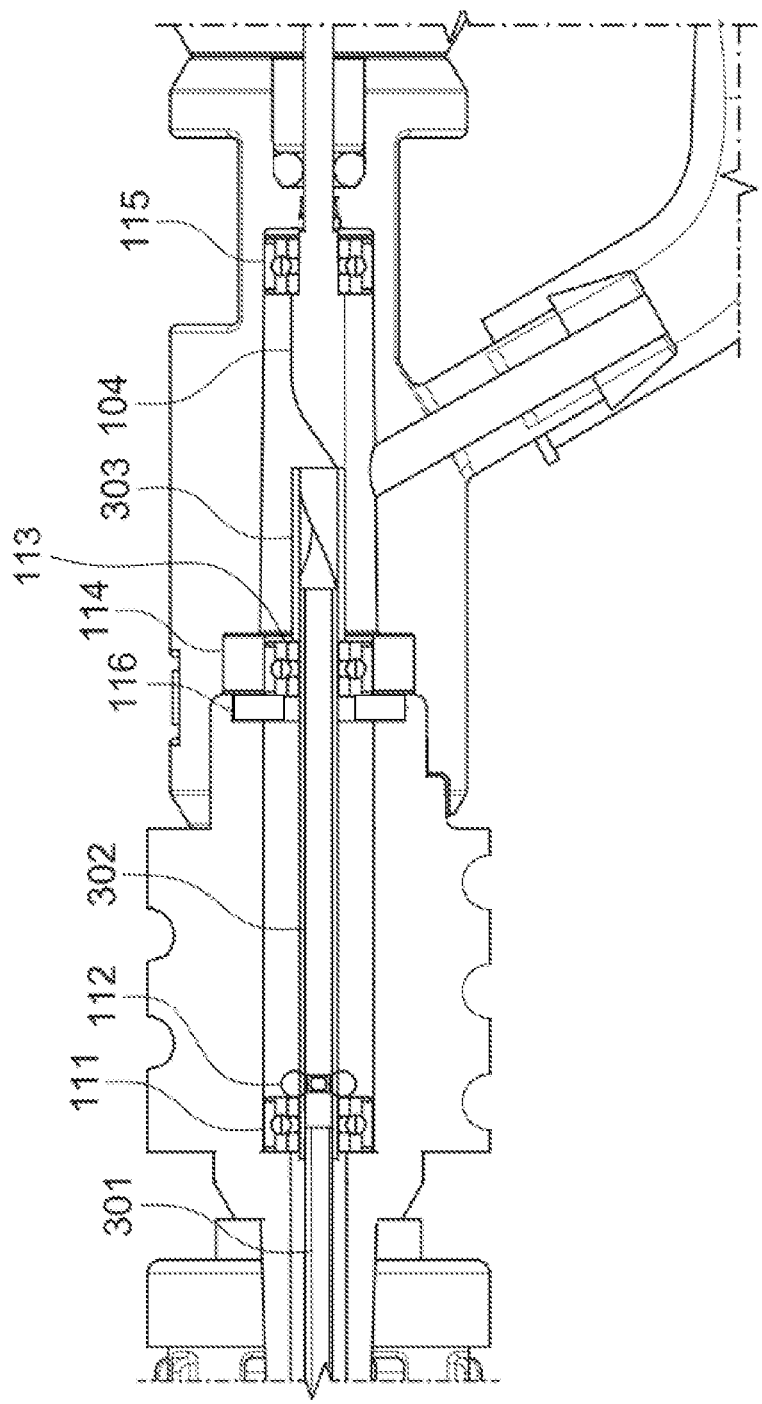

As shown in FIG. 6, the bearing 111 is disposed at a position at which the drive pipe 301 is connected to the joint pipe 302, and the bearing 113 is disposed at a position at which the joint pipe 302 is connected to the joint pipe 303 so that those pipes can be supported to rotate in a stable manner.

The bearing 111 is arranged closest to the torque unit 124. In one embodiment, the bearing 111 is a ball bearing that has an inner ring, an outer ring, and a plurality of balls therebetween, each of which is made of metal, ceramic, or plastic. Any other material suitable for a bearing may be used. In another embodiment, the bearing 111 is a busher, which is made of metal, ceramic, or plastic. For example, the bearing 111 is located on the outer surface of the joint pipe 302. The bearing 111 is located at the distal end of the joint pipe 302.

The bearing 113 is arranged proximal to the bearing 111. In one embodiment, the bearing 113 is a ball bearing that has an inner ring, an outer ring, and a plurality of balls therebetween, each of which is made of metal, ceramic, or plastic. Any other material suitable for a bearing may be used. In another embodiment, the bearing 113 is a busher, which is made of metal, ceramic, or plastic.

Additionally, the O-ring 114 is disposed outside the bearing 113. The O-ring 114 has an elastic body made of an elastic material such as rubber. In one embodiment, the bearing 113 is located on the outer surface of the joint pipe 302. The bearing 113 contacts the distal end of the joint pipe 303. The movement of the bearing 113 towards the distal end of the drive shaft 30 is restricted by a washer 116, which contacts and is held by the T-port distal cap 123.

In a first embodiment, the elastic O-ring 114 is mounted on the outer periphery of the bearing 113. Alternatively, in a second embodiment, the elastic O-ring 114 is integrated into the bearing 113 to form an outer layer thereof. In other words, in the second embodiment, the elastic O-ring 114 is formed of an inner layer including the inner ring, the outer ring, and the balls, and the outer layer made of an elastic material.

The bearing 115 is located proximal to the bearing 113. In one embodiment, the bearing 115 is a ball bearing that has an inner ring, an outer ring, and a plurality of balls therebetween, each of which is made of metal, ceramic, or plastic. Any other material suitable for a ball bearing may be used. In another embodiment, the bearing 115 is a busher, which is made of metal, ceramic, or plastic. For example, the bearing 115 is located on the aspiration drill 104.

As shown in FIGS. 4 through 6, the proximal end of the drive shaft 30 includes the joint pipe 303 and the aspiration drill 104 (or an integrated pipe thereof) between the bearings 113 and 115. In one embodiment, the outer diameter of such a portion of the drive shaft 30 is greater than the other portion of the drive shaft 30, including the joint pipe 302 inside the bearing 113 and the aspiration drill 104 inside the bearing 115. In other words, the outer diameter of the drive shaft 30 between the bearings 113 and 115 is greater than the outer diameter of the drive shaft 30 inside each of the bearings 113 and 115. For example, the outer diameter of the drive shaft 30 between the bearings 113 and 115 is 2 mm, and the outer diameter of the other portion, e.g., the drive shaft 301, the joint pipe 302, and the aspiration drill 104 inside the bearing 115, is 1.5 mm. According to this configuration, the portion of the drive shaft 30 between the bearings 113 and 115 are sandwiched and held by the side surfaces of the bearings 113 and 115, whereby the movement of the drive shaft 30 along the longitudinal direction is prevented.

Figure 7A:
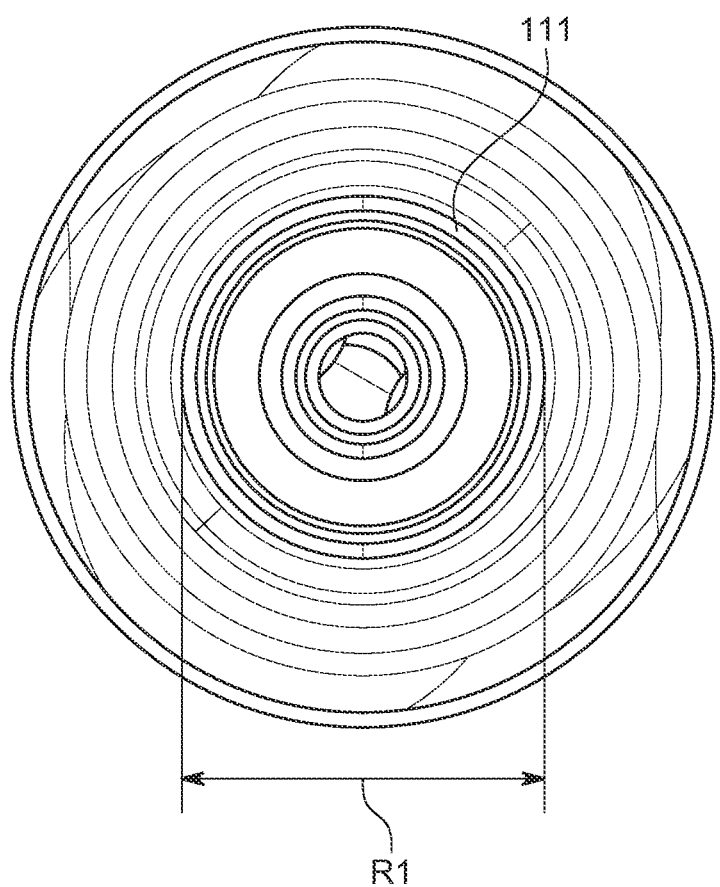
FIGS. 7A through 7C depict cross-sections of bearings according to one embodiment.
Figure 7B:
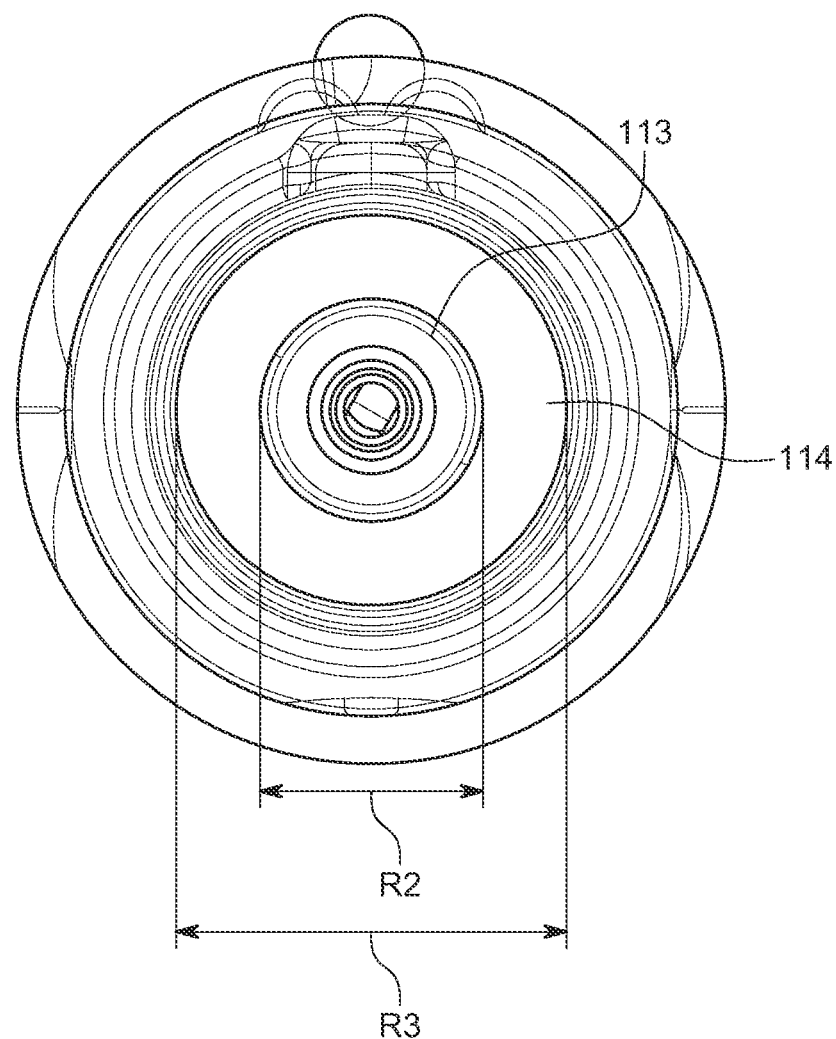
Figure 7C:
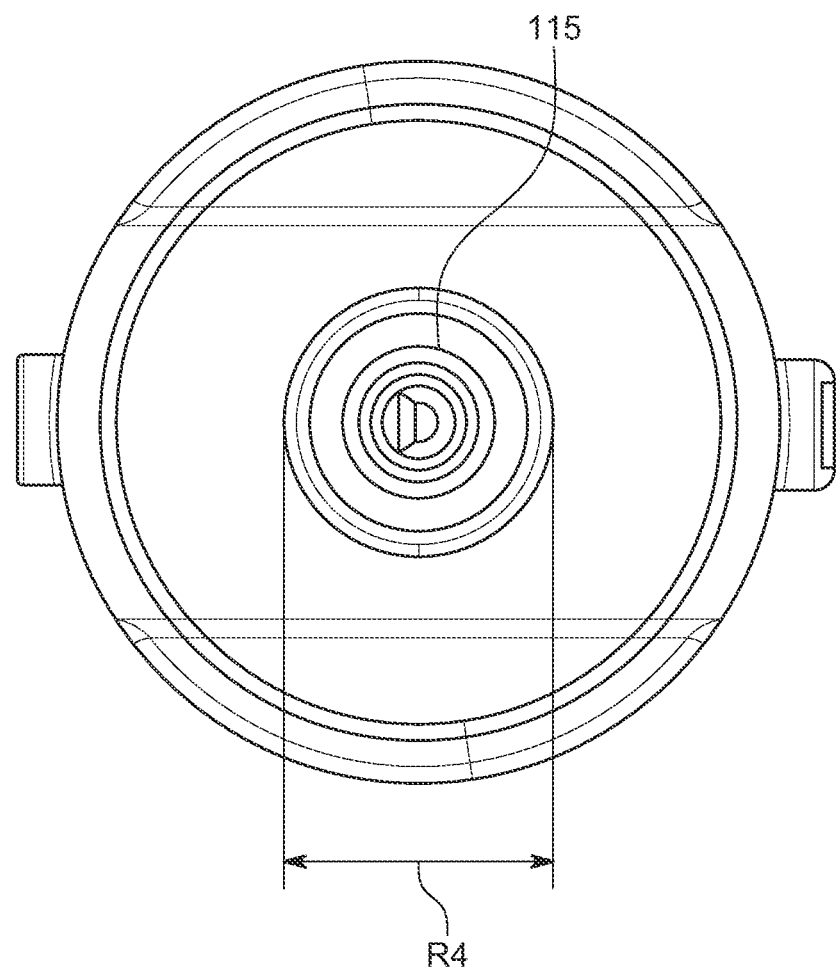
Figure 8:
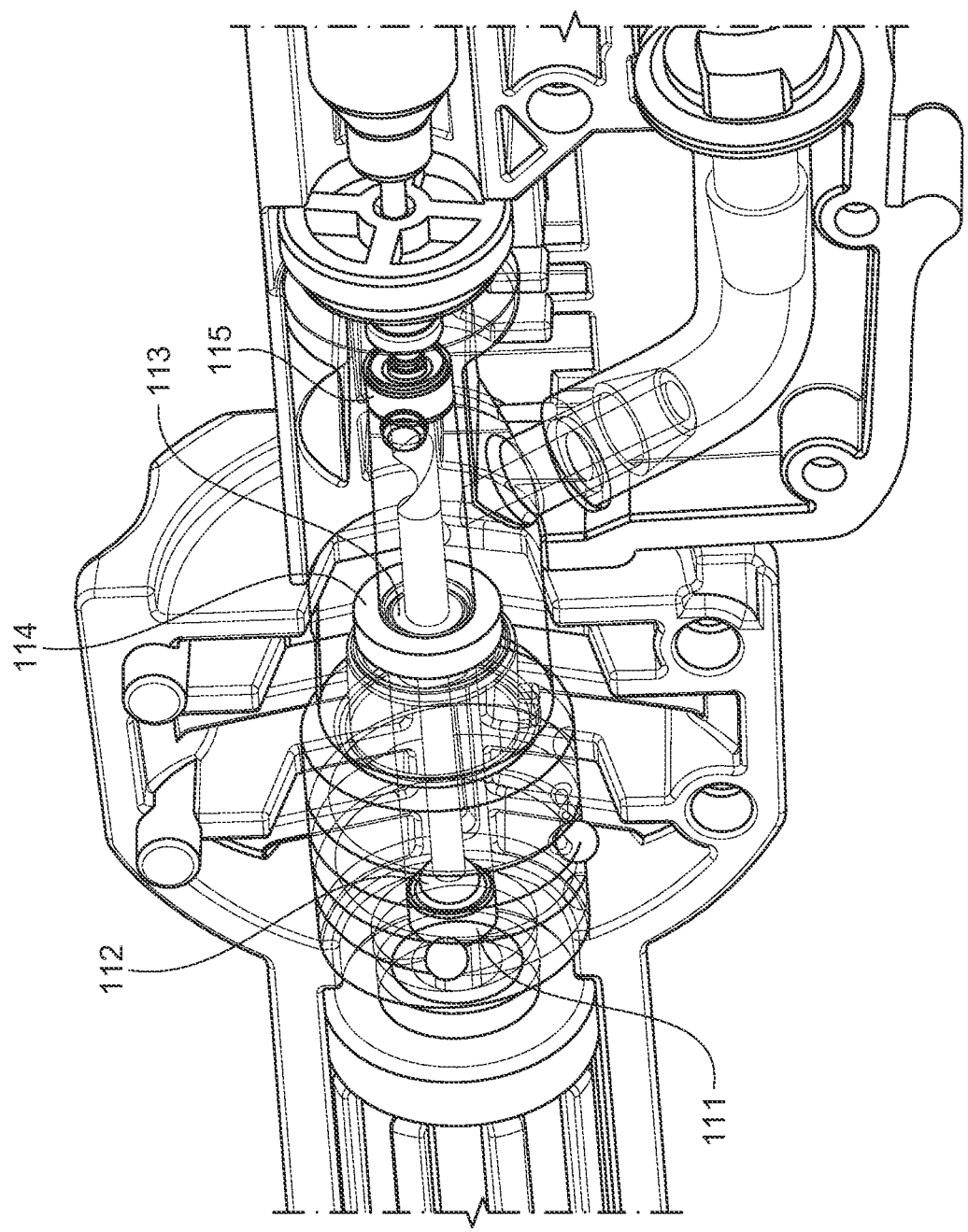
FIG. 8 depicts a perspective diagram of a hub according to one embodiment.

FIGS. 7A through 7C depict the cross sections of the bearings 111, 113, and 115, respectively. In one embodiment, the outer diameters R1, R2, and R4 of the bearings 111, 113, and 115 are substantially identical. For example, the outer diameter R1 of the bearing 111 is about 4.0 mm, the outer diameter R2 of the bearing 113 is about 4.0 mm, and the outer diameter R4 of the bearing 115 is about 4.0 mm. Those diameters R1, R2, and R4 may be different. The inner diameters of the bearings 111, 113, and 115 correspond to the outer diameters of the pipes 301 and 302 and the aspiration drill 104.

In one embodiment, the outer diameter R3 of the O-ring 114 is greater than the diameters R1, R2, and R4. For example, the outer diameter R3 of the O-ring 114 is about 7.0 mm. The inner diameter of the O-ring 114 corresponds to the outer diameter R2 of the bearing 113.

According to the above-recited embodiments, the bearing 113 and the O-ring 114 (or the bearing 113 including the O-ring 114) is provided between the drive shaft 30 and the hub 10. Since the O-ring 114 is made of an elastic material, wobble movement of the bearing 113 is prevented, resulting in reduction of vibration of the medial device 1. Additionally, the elastic O-ring 112 is attached adjacent to the bearing 111, which prevent the bearing 111 from moving along the rotation axis of the drive shaft 30. As a result, the medical device 1 can operate in a stable matter regardless of the high speed rotation of the motor.

That is claimed is:

1. A medical device for cutting substances inside a body lumen, the medical device comprising:
a flexible and elongated drive shaft including a distal portion and a proximal portion, the proximal portion including first and second pipes that are connected together, the first pipe located on a distal side of the second pipe;
a cutting member connected to the distal portion of the drive shaft to be rotatable with the drive shaft; and
a hub located at the proximal portion and supporting the drive shaft, the hub including:
a first bearing mounted on one of the first and second pipes of the drive shaft and an elastic ring that is made of an elastic material on an outer periphery of the first bearing,
a second bearing mounted on the drive shaft on a proximal side of the first bearing, and
a third bearing mounted on the drive shaft at a distal end of the first pipe, wherein
the drive shaft includes a lumen through which the substances cut by the cutting member are transported from the distal portion side thereof to the proximal portion side thereof and discharged at a location of the drive shaft that is between the first and second bearings.

2. The medical device according to claim 1, wherein the first bearing is a ball bearing that includes an inner ring, an outer ring, and a plurality of balls therebetween, and the elastic ring is mounted on the outer ring between the outer ring and an interior surface of the hub.

3. The medical device according to claim 1, wherein the first bearing is at a position at which the first and second pipes are connected.

4. The medical device according to claim 1, wherein the second pipe includes a hole from which the substances are aspirated.

5. The medical device according to claim 1, wherein the hub further includes an elastic O-ring that contacts the third bearing at a proximal side thereof.

6. The medical device according to claim 1, wherein an outer diameter of the elastic ring is greater than an outer diameter of the third bearing.

7. The medical device according to claim 1, further comprising:
an outer shaft surrounding the drive shaft, wherein
the hub includes:
a knob connected to the outer shaft, independently rotatable with respect to the drive shaft, and surrounding the third bearing.

8. A medical device for cutting substances inside a body lumen, the medical device comprising:
a flexible and elongated drive shaft including a distal portion and a proximal portion, the proximal portion including first and second pipes that are connected together, the first pipe located on a distal side of the second pipe;
a cutting member connected to the distal portion of the drive shaft to be rotatable with the drive shaft; and
a hub located at the proximal portion and supporting the drive shaft, the hub including
a first bearing mounted on one of the first and second pipes of the drive shaft, the first bearing including an inner layer and an outer layer that is made of an elastic material,
a second bearing mounted on the drive shaft on a proximal side of the first bearing, and
a third bearing mounted on the drive shaft at a distal end of the first pipe, wherein
the drive shaft includes a lumen through which the substances cut by the cutting member are transported from the distal portion side thereof to the proximal portion side thereof and discharged at a location of the drive shaft that is between the first and second bearings.

9. The medical device according to claim 8, wherein the inner layer of the first bearing includes an inner ring, an outer ring, and a plurality of balls therebetween.

10. The medical device according to claim 8, wherein the first bearing is at a position at which the first and second pipes are connected.

11. The medical device according to claim 8, wherein an outer diameter of the second pipe is larger than an outer diameter of the first pipe.

12. The medical device according to claim 8, wherein the hub further includes an elastic O-ring that contacts the third bearing at a proximal side thereof.

13. The medical device according to claim 8, wherein an outer diameter of the first bearing is greater than an outer diameter of the third bearing.

14. The medical device according to claim 8, further comprising:
- an outer shaft surrounding the drive shaft, wherein the hub includes:
    - a knob connected to the outer shaft, independently rotatable with respect to the drive shaft, and surrounding the third bearing.

\* \* \* \* \*